(12) United States Patent
Aarestad et al.

(10) Patent No.: US 12,083,036 B2
(45) Date of Patent: *Sep. 10, 2024

(54) CHAMBER CUSHION, SEAL AND USE THEREOF

(71) Applicant: SOMMETRICS, INC., San Diego, CA (US)

(72) Inventors: Jerome K. Aarestad, Escondido, CA (US); Kent Gandola, San Diego, CA (US); David Giuntoli, San Diego, CA (US); Jeff Mullally, La Mesa, CA (US)

(73) Assignee: SOMMETRICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/982,381

(22) Filed: Nov. 7, 2022

(65) Prior Publication Data

US 2023/0055975 A1 Feb. 23, 2023

Related U.S. Application Data

(60) Provisional application No. 62/260,211, filed on Nov. 25, 2015.

(51) Int. Cl.
*A61H 9/00* (2006.01)
*A61F 5/56* (2006.01)
*A61F 13/00* (2006.01)

(52) U.S. Cl.
CPC .............. *A61F 5/56* (2013.01); *A61H 9/0057* (2013.01); *A61F 2013/00174* (2013.01); *A61H 2201/1609* (2013.01); *A61H 2201/165* (2013.01); *A61H 2205/026* (2013.01); *A61H 2205/04* (2013.01)

(58) Field of Classification Search
CPC .. A61H 9/0057; A61H 2009/0064; A61F 5/56
See application file for complete search history.

(56) References Cited

U.S. PATENT DOCUMENTS

| 5,343,878 | A | 9/1994 | Scarberry et al. |
| 7,182,082 | B2 | 2/2007 | Hoffrichter |
| 7,762,263 | B2 | 7/2010 | Aarestad et al. |
| 9,820,881 | B2 | 11/2017 | Aarestad et al. |
| 11,324,626 | B2 | 5/2022 | Aarestad et al. |
| 11,491,044 | B2 | 11/2022 | Aarestad et al. |
| 2008/0163875 | A1 | 7/2008 | Aarestad et al. |
| 2011/0066086 | A1 | 3/2011 | Aarestad et al. |
| 2014/0144450 | A1 | 5/2014 | Aarestad et al. |

*Primary Examiner* — LaToya M Louis
(74) *Attorney, Agent, or Firm* — Michael A. Whittaker

(57) ABSTRACT

A device and method for creating and/or maintain an obstruction free upper airway passage. The device configured to fit under the chin of a subject adjacent to the subject's at an external location corresponding approximately with the subject's internal soft tissue associated with the neck's anterior triangle. The device including structural elements designed to optimize comfort, compliance and seal achieved through minimizing the pressure variation along the contact surface of the cushion element. The structural elements of the cushion may include a fluidly sealed chamber that may vary in thickness and width, a compressible elastic foam contained within the fluidly sealed chamber a ribbon layer backing the elastic foam contained within the fluidly sealed chamber and an adhesive layer disposed on the outer surface of the fluidly sealed chamber of the therapy device designed to contact the skin of the subject.

5 Claims, 11 Drawing Sheets

FIG. 7A
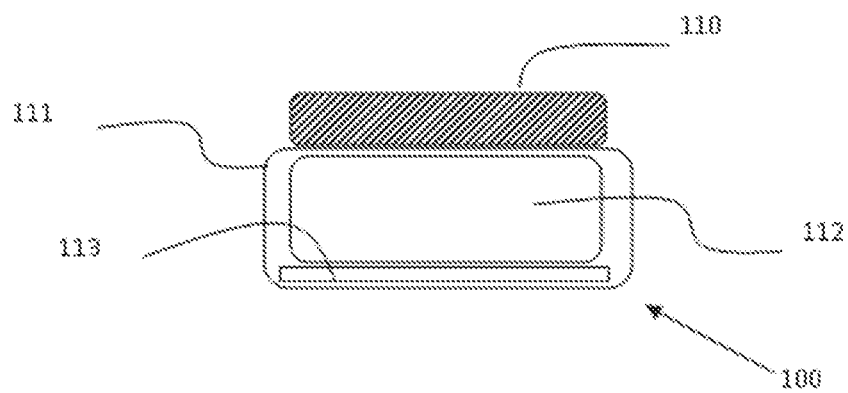
FIG. 7B
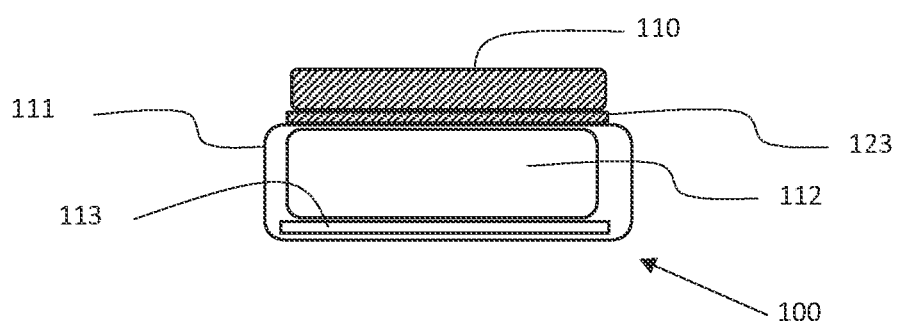
FIG. 7b

CHAMBER CUSHION, SEAL AND USE THEREOF

CROSS-REFERENCE TO RELATED APPLICATIONS

The present application is a continuation of U.S. patent application Ser. No. 15/360,419, filed Nov. 23, 2016, now U.S. Pat. No. 11,491,044, which claims priority to U.S. Provisional Application No. 62/260,211, filed Nov. 25, 2015, which is hereby incorporated by reference in its entirety.

BACKGROUND OF THE APPLICATION

The following discussion of the background of the invention is merely provided to aid the reader in understanding the invention and is not admitted to describe or constitute prior art to the present invention.

The external application of negative pressure to patients for palliative or therapeutic purpose is well established in the medical arts.

U.S. Pat. Nos. 5,343,878, 7,182,082, and 7,762,263 describe various devices which purport to utilize external application of negative pressure upon the external neck surface of patients. A therapeutic appliance is typically provided that has a surface which is configured to enclose an external area of the throat (the term "throat" as used herein referring to the anterior portion of the neck extending approximately from the chin to the top of the sternum and laterally to a point posterior to the external jugular vein) overlying a portion of the upper respiratory passage. In certain embodiments, these appliances can provide a chamber (e.g., a hollow space filled with air molecules) lying between the interior surface of the chamber and the throat. The therapy appliance is operably connected to an air pump which is configured to produce a partial vacuum in this chamber. Application of a therapeutic level of negative pressure in the chamber elicits movement of the upper airway and may alleviate conditions such as snoring, sleep apnea, and full or partial airway collapse for example.

In these "negative pressure" therapeutic apparatuses and methods it is difficult to obtain a proper and comfortable fit between the apparatus and the patient to create and maintain the differential negative pressure (relative to atmospheric pressure for example) at the desired location on the patient. This is particularly true as the devices are intended for daily wear for many hours; thus, any points of high pressure soon become too uncomfortable for continued use. Further, success of these negative pressure therapies is optimized by a device's ability to accommodate (flex, bend, flow, etc.) varying anatomical features (i.e. device compliance). Device compliance, also maximizes user participation through a good comfortable interface between the device and the user. Finally, the device should also accommodate movement to different sleeping positions without loss of seal.

BRIEF DESCRIPTION OF THE INVENTION

It is an object of the invention to provide a cushion element adapted to form a conforming sealing surface between a device that is intended to attach and seal to a patient's external tissue, such as a face, a neck, an area surrounding a wound, etc. This cushion element is particularly suited for forming a sealed chamber that is configured for the administration of negative pressure to a targeted therapy on the external tissue of an individual. By "external area" as used herein, this refers to a portion of the external skin surface of the individual. in various embodiments, the cushion element is configured to provide optimized fitting parameters, for example, seal, comfort and local device compliance throughout all points of contact. This is preferably achieved by minimizing the contact pressure differential from one point of contact on the skin of a patient to another through design features of the cushion element of a negative pressure therapy device.

In a first aspect, the present invention provides therapy devices configured for the administration of negative pressure upon the external surface of the individual. These therapy devices comprise:

a vessel configured to define a chamber at an external location approximately at the internal soft tissue of the individual corresponding to the anterior triangle of the neck;

a cushion element defining a contact area between the individual and the vessel, the cushion element comprising a first surface thereof configured to make contact with the skin of the individual when the therapy device is mated to the individual, and a second surface there of that is distal from the first surface relative to the contact area and that, together with the first surface, forms a fluidly sealed chamber;

a non-flowing material positioned within the fluidly sealed chamber, the non-flowing material configured to provide mechanical support to the fluidly sealed chamber to prevent regional collapse of the fluidly sealed chamber when the therapy device is mated to the individual and a therapeutic level of negative pressure is applied within the vessel;

a ribbon layer positioned to the non-flowing material on a surface thereof that is distal from the first surface relative to the contact area which is configured to displace the load of the fluidly sealed chamber edge over the second surface when a therapeutic level of negative pressure is applied, wherein cushion surface is configured to approximately conform to a contact area defined by approximately the gonion on one side of the mandibular body, across the mental protuberance, and to the opposite gonion of the mandibular body, and from approximately the gonion on one side of the mandibular body to a position on the neck at the level of the thyroid cartilage, and to the opposite gonion of the mandibular body.

In a related aspect, the present invention relates to devices configured for the administration of negative pressure upon the external surface of the individual, comprising:

a vessel configured to define a chamber at an external location approximately at the internal soft tissue of the individual corresponding to the anterior triangle of the neck;

a cushion element defining a contact area between the individual and the vessel, the cushion element comprising a first surface thereof configured to make contact with the skin of the individual when the therapy device is mated to the individual, and a second surface there of that is distal from the first surface relative to the contact area and that, together with the first surface, forms a fluidly sealed chamber;

An adhesive layer positioned on the exterior of said first surface to make contact with the skin of the individual when the therapy device is mated to the individual, a non-flowing material positioned within the fluidly sealed chamber, the non-flowing material configured to provide mechanical support to the fluidly sealed chamber to prevent regional collapse of the fluidly sealed chamber when the therapy device is mated to the individual and a therapeutic level of negative pressure is applied within the vessel;

a ribbon layer positioned to the non-flowing material on a surface thereof that is distal from the first surface relative to the contact area which is configured to displace the load of the fluidly sealed chamber edge over the second surface when a therapeutic level of negative pressure is applied, wherein cushion surface is configured to approximately conform to a contact area defined by approximately the gonion on one side of the mandibular body, across the mental protuberance, and to the opposite gonion of the mandibular body, and from approximately the gonion on one side of the mandibular body to a position on the neck at the level of the thyroid cartilage, and to the opposite gonion of the mandibular body.

In certain embodiments, the first surface of the cushion element and the second surface of the cushion element are formed as separate surfaces that are affixed to one another to form a peripheral joining surface, wherein the peripheral joining surface is configured to not contact the individual when the therapy device is mated to the individual and a therapeutic level of negative pressure is applied within the vessel. By way of example, the first surface of the cushion element and the second surface of the cushion element may be formed as separate surfaces that are affixed to one another by RF welding. The first surface of the cushion element and the second surface of the cushion element may be formed from a flexible thermoplastic material such as a thermoplastic polyurethane.

As described hereinafter, the term "fluidly sealed" refers to a chamber that retains the fluid contained within the chamber for a period of time required for normal use of the chamber. In various embodiments, the fluidly sealed chamber may comprise one or more of the following fluid sealed within the chamber: a gas (e.g., air), a gel, a particulate material (e.g., microspheres), a liquid, a foam (e.g., an open cell foam), etc. This list is not meant to be limiting. As described hereinafter, one or more materials within the fluidly sealed chamber may be selected to provide a non-flowing material in order to prevent collapse of the fluidly sealed chamber when in use. Such a non-flowing material may be in the form of an open cell foam having an indentational force deflection (IFD) of about 8-40 lbs/50 in$^2$, and preferably an indentational force deflection (IFD) of about 12-30 lbs/50 in$^2$ or about 18-22 lbs/50 in$^2$. The term "about" as used herein refers to +/−10% of a specified value.

In certain embodiments, the contact area of the cushion element comprises a gel material applied thereto. By way of example, a gel material may be applied to the contact area to form a tacky surface in order to resist movement of the cushion element relative to the skin of the wearer.

As described hereinafter, a cushion element is preferably configured to provide an approximately constant contact pressure across the entire contact area between the individual and the vessel when the therapy device is mated to the individual and a therapeutic level of negative pressure is applied within the vessel. This contact pressure may preferably be about 1.1 to 1.3 times the negative pressure within the fluidly sealed chamber. In certain embodiments, the perpendicular width of the contact area is varied along the peripheral axis of the contact area such that, when the therapy device is mated to the individual and a therapeutic level of negative pressure is applied within the vessel, the approximate contact pressure applied to the skin surface is approximately 1.2 times the negative pressure within the vessel.

In related aspects, the present invention relates to methods of applying negative pressure therapy to an individual in need thereof, comprising mating a therapy device as described herein to the individual, and applying a therapeutic level of negative pressure within the vessel, thereby increasing patency of the airway of the individual. Such methods can be for treatment of sleep apnea; for treatment of snoring; for treatment of full or partial upper airway collapse; for treatment of full or partial upper airway obstruction; for negative pressure treatment of a wound caused by, for example an injury or a surgery; etc.

BRIEF DESCRIPTION OF THE DRAWINGS

FIG. 7A is a cross-sectional view 117 of an illustrative embodiment of the cushion element 100 containing an adhesive layer 110, outer layer of the fluidly sealed chamber 111, the foam layer element 112 and ribbon layer element 113.

FIG. 7B is a cross-sectional view 117 of an illustrative embodiment of the cushion element 100 containing an adhesive layer 110, a primer layer 123, the outer layer of fluidly sealed chamber 111, the foam layer element 112 and the ribbon layer element 113.

DETAILED DESCRIPTION OF THE INVENTION

Figure 1:
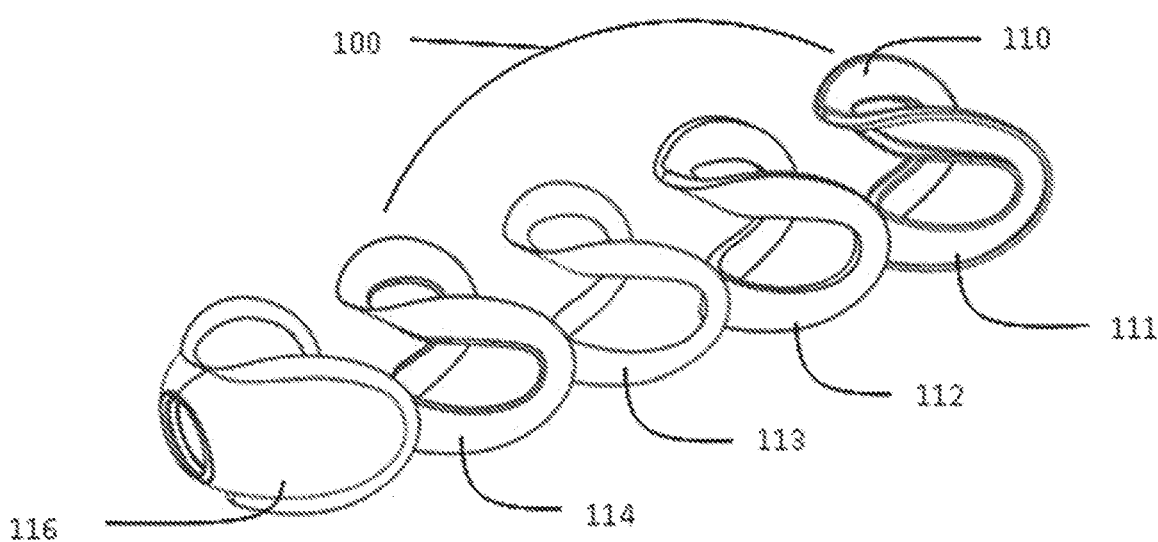
FIG. 1 is an exploded view of an illustrative embodiment of the vacuum chamber/dome 116, including cushion element 100, with the adhesive layer 110, urethane outer layer of the fluidly sealed chamber 111, foam layer 112, ribbon layer 113, and inner urethane layer of the fluidly sealed chamber 114.
Figure 2:
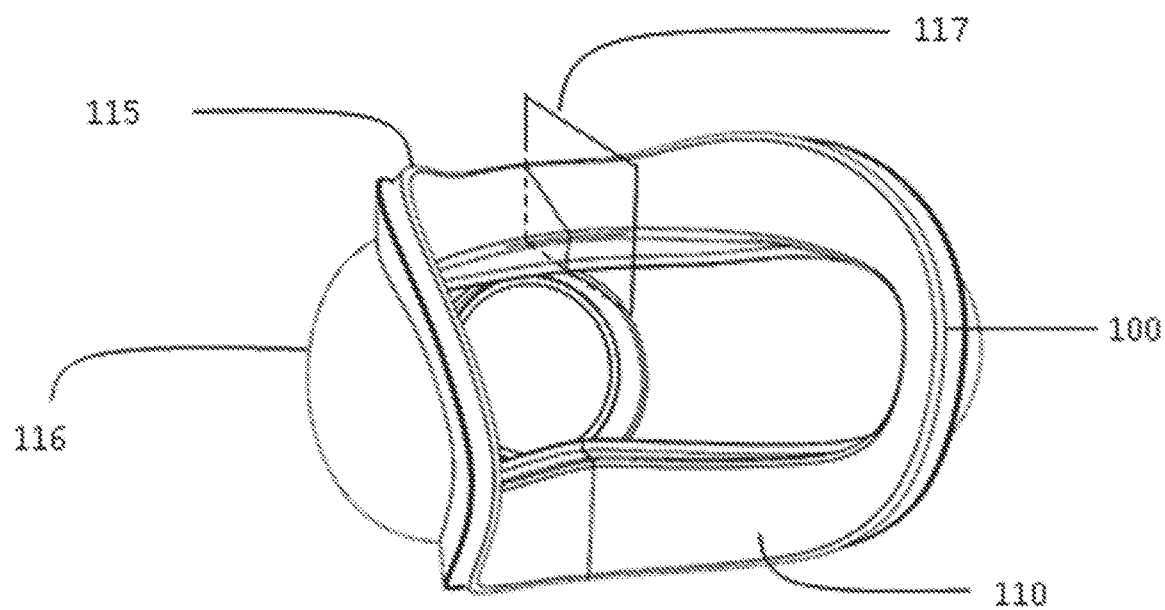
FIG. 2 is a view of an illustrative embodiment of the vacuum chamber/dome 116, with cushion element 100, with the adhesive layer 110, peripherally joined surface(s) 115 and location of cross-sectional view 117.

The present invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the present invention. The examples used herein are intended merely to facilitate an understanding of ways in which the invention may be practiced and to further enable those of skill in the art to practice the invention. Accordingly, the examples should not be construed as limiting the scope of the invention. In the drawings, like reference numerals designate corresponding parts throughout the several views.

In the present invention, a cushion element is designed for a negative pressure therapy device that maximizes comfort and seal efficiency ultimately optimizing device efficacy and user compliance. The negative pressure therapy device is described below for use in the opening of the upper airway when placed upon the neck of a subject over a surface corresponding to approximately the upper airway of the subject. This exemplary application of the technology is not meant to be limiting. The cushion element portion of the devices described herein is configured to provide for regional load equalization over the interface between a negative pressure therapy device and the three dimensionally varying skin surface of the user so as to maintain a near uniform contact pressure over this non-uniform surface.

In particular, the therapy device referred to herein relates but is not limited to an external therapy appliance for relieving upper airway obstruction. U.S. patent application Ser. Nos. 12/002,515, 12/993,311 and 13/881,836 which are hereby incorporated by reference in their entirety including all tables, figures and claims, describes a therapy appliance for relieving airway obstruction. Increasing the patency of the upper airway of an individual alleviates conditions such a snoring, sleep apnea, full or partial upper airway collapse. As described therein, a device is configured to fit under the chin of a user at an external location corresponding to the soft tissues overlying the upper respiratory passages of the neck.

Surface variation of the therapy site, both permanent and occasional (ie, the shape of the mandible, transition points from neck to mandible, tissue types, scars, facial hair and/or skin blemishes differential forces applied to different portions of the seal caused by movement of the wearer, etc.) can undesirably disrupt the seal between the negative pressure therapy device and user. The present invention provides devices, systems and methods of use that can accommodate varying facial contours and features, and adapt to movement, resulting in greater comfort, reduced vacuum leakage and improved therapeutic efficacy.

The cushion element of the sealing surface is adapted to have sectional properties that allow for flexibility and uniform regional compliance. As used herein, "uniform regional compliance" refers to a property of the cushion element that permits the cushion element to "mold" itself to a surface and or surface variation on the contact surface with the wearer. As described hereinafter, this uniform regional compliance is provided, in part, by the sectional properties or features associated with a region on the cushion element.

The cushion element comprises a fluidly sealed chamber; and a foam layer and/or a semi-rigid ribbon layer housed within the fluidly sealed chamber. The term "fluidly sealed" refers to a chamber that retains the fluid contained within the chamber for a period of time required for normal use of the chamber. By way of example, a latex balloon is "fluidly sealed" to helium if normal use of the balloon is for 6 hours, despite the fact that over time that helium may ultimately leak from the balloon, and despite the fact that the balloon may burst if put under abnormal conditions.

Optionally an adhesive layer is located on the surface of the cushion element that makes contact with the user. These elements are configured to maintain an approximate uniform contact pressure with minimized pressure variations along the skin of an individual through all points of contact of the therapy device on a patient. By "minimized pressure variation" means a pressure at any point between the contact surface of the cushion element and the patient's tissue varies by no more than 20%, and preferably no more than 10% or 5%, from the average pressure across the entire contact surface. The outer contact surface, as used herein, is the surface of the cushion element of the therapy device that makes contact with the skin of the individual forming the contact and sealing surface of the therapy device.

In certain embodiments, the cushion element of the invention provides the contact interface of a negative pressure therapy device configured to conform to the external area of the neck approximately corresponding to the anterior triangle of the neck. Most preferably, the cushion element is configured to follow the contour of the therapy device which is designed to approximately conform to an individual from approximately the gonion on one side of the mandibular body, across the mental protuberance, and to the opposite gonion of the mandibular body and further configured to approximately conform to an individual from approximately the gonion on one side of the mandibular body to a position on the neck near the level of the thyroid cartilage, and to the opposite gonion of the mandibular body.

In certain embodiments, the negative pressure therapy device of the present invention is a chamber, approximately a dome, oval in appearance, with a curvature from the middle of the dome that creates a collar to cover an area over the upper airway of an individual. In preferred embodiments the negative pressure therapy device contains structural elements adapted to guide correct placement and orientation of the device on the user, for example a chin cup element. As used herein a "chin cup" refers to a discreet feature on the negative pressure therapy device which provides a recess configured to receive the chin of the wearer when the negative pressure therapy device is properly mated to the wearer. During application of the negative pressure therapy device, the chin cup provides a consistent point of reference on which the negative pressure therapy device can mate with the wearer. The shape of the chin cup may vary to allow for anatomical variation in patients. For example, the chin cup may be somewhat deeper for use in a subject having mandibular prognathia; somewhat shallower for use in a subject having mandibular retrognathia; or somewhat large in volume for a subject having macrogenia.

In various embodiments, the present invention comprises a symmetric vacuum chamber with a flat contact surface adapted to fit to a flat uniform surface and to provide minimized pressure variation throughout all points of contact when a vacuum is applied. In other various embodiments, the present invention comprises a vacuum chamber with a contact surface configured to adapt to the inherent anatomical variations of an individual's face. The curved, "wraparound" shape that the negative pressure therapy device must assume can cause the "station load" through different contact points to vary in the absence of the design features described herein. For example, absent a feature or features designed to accommodate for station load variation, at points furthest from the center of the dome of the therapy device, toward the narrow end portions of the oval, the station load decreases due to a lesser vacuum cross section over the contact point(s). As used herein, "station load" is the force or pressure which is applied at a discreet area of contact of the device (a "station") on the skin of an individual when the device is mated to the individual and a therapeutic level of negative pressure is applied.

As discussed herein, the cushion element of the instant invention forms the interface between the dome/chamber of the therapy device and the contact surface of the individual. The cushion element comprises structural features that provide minimized pressure variation at stations where contact pressure variation can occur as a result of either anatomical variation, tissue variation, inherent therapy device design, and or movement during usage. The cushion element thereby providing features to the therapy device to minimize peak contact pressure values, minimize the variance from station to station and equalize the contact pressure of the therapy device when a therapeutic level of negative pressure is applied to provide an effective seal.

The term "seal" as used in this context is not to necessarily imply that a perfect seal is formed between the therapy device and the contact surface of the individual. Rather, a "seal" is a portion of the device which mates to the wearer and maintains a therapeutic level of vacuum. A certain amount of leakage at the seal may be tolerated so long as the desired negative pressure can be achieved and maintained. Preferred operational vacuum levels are in a range of between 7.6 cm to about 61 cm of water. Preferred forces applied to the user's neck tissues in order to assist in opening the upper airway passages are in a range of about 0.5 kilogram to about 6.68 kilograms.

The chamber enclosed by the dome provides a finite volume which must be evacuated to deliver the desired partial vacuum level. Once generated, the partial vacuum will decay at a rate which is primarily controlled by leakage of air into the chamber past the seal and or features integrated into the dome to provide airflow. In certain embodiments, the chamber encloses a volume of between 0.5 and 12 in$^3$. Preferably, the leakage is no more than between 0.005 and 0.5 in$^3$/min, and most preferably between about 0.01 and 0.1 in$^3$/min.

The present invention provides both sufficient regional, and overall, compliance of the cushion element such that local bottoming/regional collapse of the cushion element does not occur under load. As used herein, "regional compliance" of the cushion element refers to the ability of individual stations of the cushion element to accommodate a therapeutic level of vacuum without complete compression of the fluidly sealed chamber at that station. As used herein, "overall compliance" of the cushion element refers to the ability of the cushion element to accommodate a therapeutic level of vacuum without complete compression of the fluidly sealed chamber. Further, bottoming or "regional collapse", as used herein, is defined as a complete or near complete compression of the fluidly sealed chamber and material within such that its resistance to further compression is no longer possible. This results in a hardening of supporting structure(s) by the flexible portions of the cushion element under a heavy load, and loss of comfort by the wearer.

The cushion element is preferably a certain thickness and width to achieve the desired cushion contact pressure properties and avoid regional collapse. This is accomplished, in certain aspects, by the cross-section of the fluidly sealed chamber being of a substantially rectangular shape. The perpendicular width (width) component of the cushion may vary along the peripheral axis of the contact area of the cushion element to accommodate for station load variations due to non-uniform shape of the therapy device that contains a dome, that is oval in shape and further contains a central bend to accommodate the mating surface on the neck of the patient corresponding to approximately the upper airway and maintain a constant contact pressure of the negative pressure therapy device.

Thickness of the cushion may also vary along the contact surface of the therapy device to accommodate for anatomical variation. As used herein, thick or thin, describes the distance between the surface of the cushion contacting the individual and surface of the cushion contacting the dome of the vacuum chamber of a negative pressure therapy device. As used herein, perpendicular width describes the distance between the inner and outer edges of the cushion element. These dimensions gives the cushion truss-like properties such that if the cushion element is too thin, though it may be very flexible it will have little to no cushioning properties, can bottom out creating point(s) of high contact pressure resulting in leaks and/or discomfort. If the cushion element is too thick it will affect its ability to change direction for example be unable to conform to the acute change from the surface of the neck over the mandible toward the ear for example and further allow for an undesirable level of sheer or lateral movement.

In a similar fashion, if the width of the cushion element is too small it can create a point(s) of high pressure and too wide it may create unnecessary bulk affecting fit and effective therapy area. In a preferred embodiment of the device the cushion element is approximately 28 mm wide and approximately 6 mm thick, where this aspect ratio minimizes positional instability and optimizes flexibility.

"Contact pressure" as used herein, refers to a pressure value dependent on the vacuum present as well as the perpendicular width and surface area of the contact surface. A larger "perpendicular width" of a contact surface (meaning the direction that is perpendicular to the longest axis of the contact surface, which longest axis may be curved) will have a lower overall contact pressure under the same vacuum pressure as a contact surface with a smaller perpendicular width due to the increased surface area at that particular station of the contact surface. Therefore in regions where the dome station pressure load is low, the contact surface of the cushion can be designed to be of a smaller perpendicular width to effectively increase and "balance" the contact pressure and in regions where the dome station pressure is high, the contact surface of the cushion can be designed to be of a larger perpendicular width to effectively decrease and balance the contact pressure where the dome station load is high.

The term "balance" refers to the contact pressure of the therapy device being approximately equal at each station of the contact surface. This contact pressure is proportional to therapy vacuum levels relative to the contact area of the therapy device. For example, in a comparison, a larger contact area vs a smaller contact area, under the same therapy vacuum level will provide for lower contact pressure of the therapy device respectively. In an embodiment of the invention the contact area of the cushion relative to the therapy area provides for a contact pressure that may range from approximately 0.9 to approximately 1.5 times the vacuum level and in a preferred embodiment the contact pressure of the cushion element is approximately 1.2 times greater than therapy vacuum levels.

The cushion element provides a fluidly sealed chamber made of a thermoplastic material that may include, for example, thermoplastic polyurethane (TPU), PVC, PVDC, EVA, PET, nylon and other resins. In a preferred embodiment the fluidly sealed chamber is made of TPU. The TPU film is of a thickness that ranges approximately from about six to about twelve thousands of an inch and subsequent thermal forming may draw down final thickness to as low as about two thousands of an inch.

The urethane material may be selected from a group that are lubricant, wax and/or inorganic filler-free, thus allowing for better adhesion of, for example, an adhesive gel-like layer. The TPU film, further may also contain a matte or textured surface to also aid in adhesion of an adhesive gel-like layer. The fluidly sealed chamber may be formed using multiple sheets of urethane film that are cut to span the contact area of a therapy device. The multi sheet method allows for the insertion of additional cushioning elements or features and the sheets are affixed to one another using any suitable method, for example the use of pressure sensitive adhesives, gluing and/or RF welding.

In preferred embodiments the TPU layers are affixed to one another to create a peripheral joining surface. As used herein, "peripheral joining surface" refers to the edge created by the joining of the TPU layers that create the fluidly sealed chamber. In preferred embodiments the peripheral joining surface is configured furthest away from contact area of the therapy device such that when the therapy device is mated to an individual and a therapeutic level of negative pressure is applied within the vessel, the peripheral joining surface does not make contact with the skin. The peripheral joining surface may be sealed using RF welding. The term "RF Welding" refers to a discreet process of permanently bonding thermoplastic materials through the usage of electromagnetic energy to produce molecular agitation such that they melt together forming a bond as strong as the original material.

In certain embodiments the fluidly sealed chamber may contain a neutral or positive air pressure to achieve a desired cushion compliance. As used herein, "cushion compliance" is the level of displacement achievable by the cushion element of the negative pressure therapy device. In a preferred embodiment the fluidly sealed chamber contains ambient air pressure. As used herein ambient air pressure is defined as the air pressure at the location of use. In order to achieve ambient pressure of the fluidly sealed chamber at all altitudes, in certain embodiments, the fluidly sealed chamber may provide a valve or re-sealable interface for the inflation or deflation of the fluidly sealed chamber.

In certain embodiments, together or with one or more of the foregoing, a material, which will act as an adhesive layer between the cushion element of the therapy device and the user, is applied to the outer contact surface of the fluidly sealed chamber element of the cushion element. The purpose of the adhesive layer is to provide a sealing, cushioning and or sheer absorbing element to the cushion element. As used herein sheer refers to sheer strain which is a deformation of a material in which parallel surfaces can slide past one another, for example the contact surface of the cushion element and the skin of the user.

The adhesive layer further must preferentially adhere to the outer contact surface of the negative pressure therapy device and provide a sufficient level of "tack" such that a releasable mechanical anchoring of the therapy device to the skin of the user is achieved. Tack, as used herein, refers to a material device at the interface created between the adhesive layer and the device and the skin of the user at the other interface created between the user and the device.

The adhesive layer may be applied to the contact surface area of the negative pressure therapy device in any suitable method including but not limited to spraying, painting, placing, etc., in single or multiple layers to achieve the desired cushioning and sealing properties including but not limited to thickness, hardness and tack for example. In additional embodiments the adhesive layer may be single layer of a uniform thickness or a single layer of a non-uniform thickness covering the contact surface of the negative pressure therapy device. In further embodiments the adhesive layer may contain a series of parallel adhesive beads spanning the circumference of the contact surface of the negative pressure therapy device wherein the beads can be of a uniform or non-uniform thickness and of a like or varying adhesive and or gel-like material to achieve the desired cushioning and sealing properties.

In certain embodiments the adhesive layer is present on the contact surface of the negative pressure therapy device at a thickness falling within a range of approximately 0.005-0.060 inches. In certain embodiments the adhesive layer is present on the contact surface of the negative pressure therapy device at a thickness falling within a range of approximately 0.010-0.050 inches. In further embodiments the adhesive layer is present on the contact surface of the negative pressure therapy device at a thickness falling within a range of approximately 0.020-0.040 inches.

The adhesive layer may be achieved by using various materials, such as, but not limited to gel, elastomer, viscous solutions, foams and materials of the like. These materials can be of any chemical composition which provides the necessary end use properties (i.e. tack, firmness, medical clearance, etc.). These materials include, but are not limited to polyurethanes, silicones, acroylnitrile butadiene styrene (ABS), hydrogels, and the like. In preferred embodiments, the adhesive layer should have a hardness as measured by ASTM-D2240-00 (American Society for Testing Materials) of between 0 and 50, more preferable between 5 and 30 most preferable between 5 and 15. In certain embodiments the adhesive layer is made of a silicone gel material. The silicone can be any organosilicone which yields the desired properties although polydimethylsiloxane (PDMS) is often chosen.

The adhesive layer may be applied directly to the outer contact surface of the cushion element to a desired thickness or in combination with primer layer(s) and or primer layer(s) in combination with an adhesion or binding promotor layer(s) to create the adhesive layer to a desired thickness. As used herein a "primer" is a substance used as a preparatory coating, acting as a joining surface between the contact surface of the negative pressure therapy device and adhesive layer or an adhesion promoting layer and the adhesive layer. Further, an adhesion promoting layer is a substance used as a coating to preferentially adhere the adhesive layer to the contact surface of the negative pressure therapy device and or the primer layer that is applied to the outer surface of the negative pressure therapy device.

By way of example, a primer layer may be applied to the contact surface of the negative pressure therapy device to a thickness of about 0.005 inches, followed by an adhesive promoting layer to a thickness of approximately 0.005 inches, followed by the application of an adhesive layer to a thickness of approximately 0.040 inches achieving a final thickness of approximately 0.050 inches. A primer layer may be applied directly to the outer contact surface of the negative pressure therapy device followed by the application of the adhesive layer directly to the primer to a desired thickness of approximately 0.050 inches. In additional embodiments, an adhesive promoter may be applied to the contact surface of the negative pressure therapy device followed by the application of the adhesive layer to a desired thickness of approximately 0.050 inches.

In certain embodiments the adhesive layer is a gel layer. As used herein a gel layer is a layer of material that can have properties that are mostly liquid however behave like solids due to the cross-linked nature of its structure. The material chosen for the gel layer may be of a certain cohesive pliable consistency so as to mold to and conform to complex shapes for example imperfections in the skin. As used herein cohesive pliable consistency, elasticity or firmness of the gel layer is defined as the gel layer's ability to flow, mold and stretch and substantially return its original shape when not applied to a surface. The material chosen for the gel layer may also be of a certain tack so as to mechanically secure to the contact area. As used herein tack is defined as the gel's "stickiness" and is the property that allows the immediate formation of a bond on contact with another surface The adhesive layer material must adhere sufficiently to the therapeutic device such that it stays adhered to the device when the device is removed from the users' skin. Additionally must have a tack level that is chosen for appropriate performance at the users skin interface. That is, at too great a level of tack removal of the device from the skin can be difficult, painful or injurious. While insufficient tack can allow the device to move during use or allow the seal to the skin to open thereby losing the vacuum. The level of tack can be measured by a texture analyzer. For example, using a TA.XT plus with a 7 mm radius and 1 inch diameter spherical head the peak adhesion values should be in a range of 200 to 400 grams peak force more preferably 250 to 350 grams peak force and most preferably 275-325 grams peak force.

As discussed above the tack of the adhesive layer is optimized to achieve a releasable but mechanical anchor of the therapy device to the patient. In certain embodiments the contact surface of the fluidly sealed chamber is coated with a primer to preferentially anchor the adhesive layer to the negative pressure therapy device over the contact region of the user.

In certain embodiments the adhesive layer is formed from a washable silicone gel such that when washed and allowed to dry, the adhesive layer returns towards an initial tack. In certain embodiments the silicone gel is chosen from a group with properties that can be controlled including, but not limited to: cross sectional thickness, degree of crosslinking (and thereby firmness and tack) and viscosity (so as to be processable under desired conditions. As used herein viscosity is measured in cps referring to centipoise (cps) were 1 cps=0.01 g/cm/s.

In an embodiment of the invention the gel layer is a prepared from a two part platinum cured organosilicone mixture with properties equivalent to a silicone gel base having an uncatalyzed viscosity of about 20,000 cps and a crosslinker having an uncatalyzed viscosity of about 300 cps. The final firmness (cps) of the cured gel may be increased by increasing the proportion of the crosslinker in the mixture or decreased by lowering the proportion of the crosslinker in the mix. The tack of the material can be increased by decreasing the proportion of crosslinker in the mixture or decreased by increasing the proportion of crosslinker in the mix. In order to achieve the desired properties using a silicone gel base of 20,000 cps and a crosslinker of 300 cps, the ratio of silicone gel base to crosslinker may range (in parts by weight) from about 10.0:0.01 to about 10.00:10.20

In embodiments of the invention the ratio of 20,000 cps silicone gel base to 300 cps cross linker may further range from about 10.0:0.01 to about 10.0:0.5. In other embodiments of the invention the ratio of 20,000 cps silicone gel base to 300 cps crosslinker may range from about 10.0:0.01 to about 10:0.1. And in further embodiments of the invention the ratio of 20,000 cps silicone gel base to 300 cps crosslinker may range from about 10.0:0.06 to about 10:0.20

By example of the invention the silicone gel base and the crosslinker are mixed in desired ratios and placed under vacuum in order to remove any bubbles in the mixed solution (de-gassing). Following de-gassing, the silicone gel solution is applied to the contact surface of the cushion element and allowed to cure. The mixture can achieve full cure in approximately 24 hours at room temperature however in some embodiments a full cure of the silicone gel may be achieved in about 5 minutes by placing the cushion element contain the silicone gel layer at about 150° C. The cure temperature may be adjusted to suit limiting elements of the cushion, for example lower melting points of other cushion elements.

In certain embodiments the adhesive layer is made of a hydrogel. Hydrogels are a three dimensional network of crosslinked hydrophilic polymer chains that can be crosslinked either physically or chemically. Due to the hydrogel materials significant water content, hydrogels can resemble natural soft tissue more than any other type of polymeric biomaterial. In further embodiments the hydrogel layer may be found as a hydrocolloid wherein the colloid particles are hydrophilic polymers dispersed in water.

In certain embodiments the adhesive layer is made of a combination of materials applied side-by side on the outer contact surface of the fluidly sealed chamber. By way of example, a hydrogel material may be applied to the circumference of the center portion of the outer contact surface of the fluidly sealed chamber and a silicone gel material may be applied on either side peripheral to the hydrogel material. In further embodiments where a combination of materials are applied side-by-side on the outer contact surface of the fluidly sealed chamber, a silicone gel layer may be applied to the circumference of the center portion of the out contact surface of the fluidly sealed chamber and a hydrogel material may be applied to either side peripheral to the silicone gel material followed by a final application of a silicone gel material peripheral to the hydrogel material.

In certain embodiments the fluidly sealed chamber may contain features that further prevent regional collapse and bottoming. Absent local support, a fluidly sealed chamber containing only air may experience situations where the air will flow continuously away from a point of high contact pressure for example displace upon application of a force on the device or cushion causing a bottoming event. In one aspect the fluidly sealed chamber may be formed with multiple chambers to minimize the collapsing events. In preferred embodiments, the fluidly sealed chamber may contain a fill layer of a non-flowing material. As used herein, "non-flowing material" refers to a material that is restrained from movement from a location of high contact pressure to a region of low contact pressure. By way of example, water or air can be freely displaced from a region within in a balloon by squeezing of the region, provided that the material of the balloon is sufficiently compliant so as to permit the remaining volume of the balloon to expand slightly and accommodate the displaced water or air. However, if the balloon is filled with a sufficiently "solid" material, that material is restrained from such movement. The non-flowing material may be a compressible, elastic filling material that provides additional support, for example filling materials may be liquids, viscous solutions, gels, cross-linked gels, polymers, spheres, microspheres, suspensions, slurries and foams.

In preferred embodiments of the cushion, the fill layer of the fluidly sealed chamber contains a foam layer element. The foam layer element is housed inside the fluidly sealed chamber element. The foam layer element aids in the stabilization of the therapy device as well as provides cushioning against high local loads caused by anatomical protrusions into the fluidly sealed chamber and/or exterior forces for example pillows proximal to the mandible placed or moved on to by the individual during sleep. As used herein, foam is a substance that is formed by trapping pockets of gas in a liquid or solid. The foam element may be of a certain porosity, as used herein porosity is the ratio of foam-to-air often measured in Pores Per Inch (PPI) designating the number of pores in one liner inch of material. The foam element may be of open or closed cell format. As used herein, an open cell foam is a material that can exchange air or liquid upon compression or release of compression on the foam. As used herein, a closed cell foam is a material in which the gas forms discreet pockets, each completely surrounded by the solid material.

Foam is manufactured by trapping bubbles of air in a plastic material to create cells and fall in to two categories, one of flexible foams which are typically open celled foams and the other of rigid foams which are typically closed celled foams. In open celled foams, cell walls are not sealed within the foam, allowing gas to pass freely throughout and in and out of the foam. Open celled foams are categorized as foams that contain greater that 50% open cells. Closed celled foams are generally highly cross-linked polymers that prevent gas movement making for a rigid foam. In a preferred embodiment the foam element is open cell foam and of a softness so as to not override the compliance of the fluidly sealed chamber element.

The foam layer element may be chosen from a group containing specific recovery characteristics. As used herein, recovery is defined as the return of a material to its original dimension and properties after a deforming force is removed. The foam layer element may be loosely fitted or may be pre-loaded in the air-bladder element. As used herein, pre-loaded is defined by applying a stress to a material, for example the compression or overstuffing of the foam element during manufacture of the air-bladder/cushion to generate added cushion stiffness creating additional rate to add regional compliance, prevent bottoming or to prevent wrinkles of the cushion or a combination whole or in part. As used herein rate is defined as the load in pounds divided by the deflection in inches. For example, a soft spring has a low rate and deflects a greater distance under a given load In a preferred embodiment the foam layer element is a medium density, flexible polyurethane foam containing Indentational Force Deflection (IFD) of approximately 8-40 lbs/50 in$^2$. IFD is used in the flexible foam manufacturing industry to assess the "softness" of a sample of foam and measured in lbs/50 in$^2$ for 25% indentation. As used here in softness is defined as yielding readily to touch or pressure. IFD is can be determined by using ASTM Standard D3575 (American Society for Testing Materials) where typically a 100 mm thick slab of foam with an area of approximately 500 mm by 500 mm is place on a perforated surface and "warmed up" by being compressed twice to 75% strain with a circular flat indenter with a surface area of 323 cm$^2$ and then allowed to recover for 6 minutes. The IFD is then measured 1 minute after achieving 25% indentation by the indenter. In certain aspects the foam layer element is an open celled foam with an IFD of 12-30 lbs/50 in2 and in a further aspect the foam layer element is an open celled foam with an IFD of 18-22 lbs/50 in$^2$.

In certain aspects, the device contains a thin ribbon element backing the foam layer element located between the inner surface of the cushion element and the foam layer element of the apparatus. The ribbon element is made of a semi-rigid material and is cut to mimic the shape of the contact surface of the therapy device. Further, the ribbon element layer may be continuous semi-rigid element or may contain cut-outs to allow for additional flexibility at desired points. The ribbon layer element provides rigidity to the cushion element and is configured to displace the load of the vacuum chamber/dome edge across the full width of the fluidly sealed chamber and subsequently the contact surface of cushion element and contact region of the subject when a therapeutic level of negative pressure is applied. In a preferred embodiment the ribbon element is made of a medical grade, USP Class VI compliant, polystyrene material.

Elements of the cushion for example, the fluidly sealed chamber, filling material and ribbon layer may be formed freely wherein the fill material and ribbon layer within the fluidly sealed chamber contain no specific adhesion to the inside of the fluidly sealed chamber or each other. However in certain embodiments bonding of one or more interior layers may be preferable to prevent some or all of the cushion elements from moving inside the fluidly sealed chamber.

As used herein, "user compliance" is the patient's adherence to the prescribed usage of a therapy device for example the usage of a device throughout a sleep cycle.

As used herein, "device compliance" refers to the ability of the device or elements of the device to accommodate variation, for example, bending, twisting, compressing and or expanding of the device in response to device application and usage including anatomical variations of the patient.

Aspects of the device may be made of a generally rigid material. The term "generally rigid" as used herein refers to a material which is sufficiently rigid to maintain the integrity of the particular element in question. The skilled artisan will understand that a number of polymers may be used including thermoplastics, some thermosets, and elastomers. Thermoplastic materials become flowing liquids when heated and solids when cooled, they are often capable of undergoing multiple heating/cooling cycles without losing mechanical properties. Thermoset materials are made of prepolymers which upon reaction cure irreversibly into a solid polymer network. Elastomers are viscoelastic materials which exhibit both elastic and viscous properties and can be either a thermoplastic or thermoset. Common thermoplastics include PMMA, cyclic olefin copolymer, ethylene vinyl acetate, polyacrylate, polyaryletherketone, polybutadiene, polycarbonate, polyester, polyetherimide, polysulfone, nylon, polyethylene, and polystyrene. Common thermosets include polyesters, polyurethanes, duroplast, epoxy resins, and polyimides. This list is not meant to be limiting. Functional filler materials such as talc and carbon fibers can be included for purposes of improving stiffness, working temperatures, and part shrinkage.

Aspects of the device may be formed using a number of methods known to those of skill in the art, including but not limited to injection molding, machining, etching, 3D printing, etc. In preferred embodiments, the test device base is injection molded, a process for forming thermoplastic and thermoset materials into molded products of intricate shapes, at high production rates and with good dimensional accuracy. The process typically involves the injection, under high pressure, of a metered quantity of heated and plasticized material into a relatively cool mold—in which the plastic material solidifies. Resin pellets are fed through a heated screw and barrel under high pressure. The liquefied material moves through a runner system and into the mold. The cavity of the mold determines the external shape of the product while the core shapes the interior. When the material enters the chilled cavities, it starts to re-plasticize and return to a solid state and the configuration of the finished part. The machine then ejects the finished parts or products.

Those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The cushion device of the present invention comprises structural member(s) that interfaces outside a targeted therapy area of a patient. In a preferred embodiment the therapy area is that of the upper airway. The therapy device contains a vacuum chamber/dome 116 that is used to create a vacuum between an inner surface of the appliance and the skin of the upper neck/chin region. The vacuum chamber/dome 116 is secured to a cushion element 100 at a single point along the back of the cushion 119 that evenly distributes the force across all of the cushion element. The device may be formed, molded, or fabricated from any material or combination of materials. Non-limiting examples of such materials suitable for constructing the therapy appliance include plastics, metals, natural fabrics, synthetic fabrics, and the like. The device may also be constructed from a material having resilient memory such as, but not limited to, silicone, rubber, or urethane.

Figure 3:
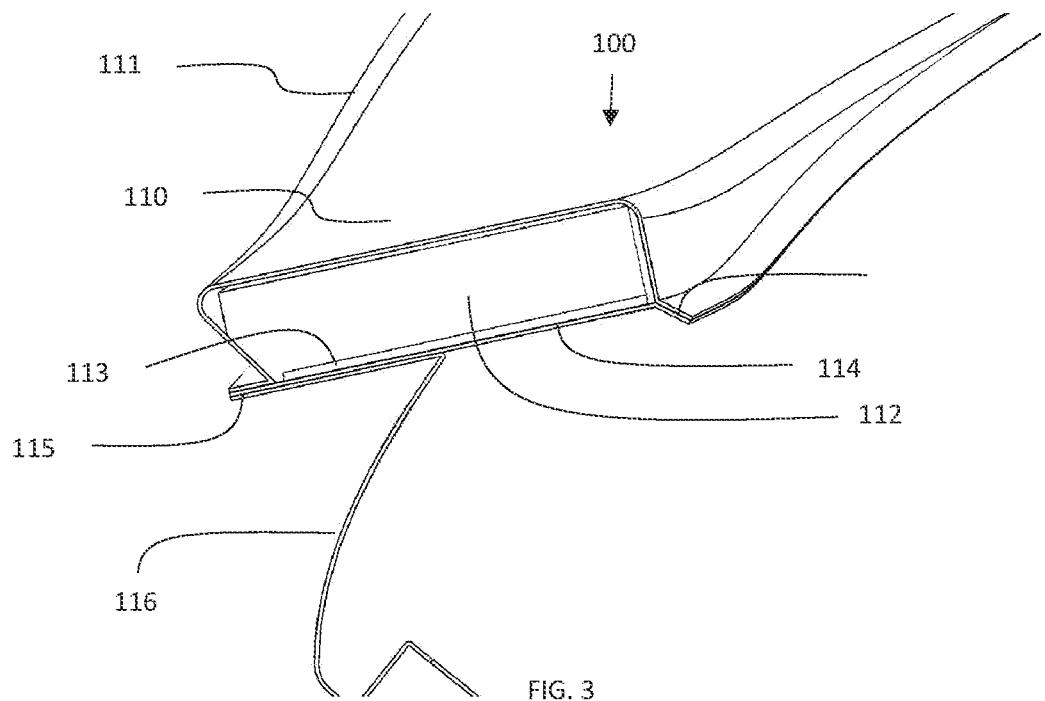
FIG. 3 is cross-sectional view 117 of an illustrative embodiment of the therapy device with the cushion element 100, with the adhesive layer 110, urethane outer layer of the fluidly sealed chamber 111, foam layer 112, ribbon layer 113, urethane inner layer of the fluidly sealed chamber 114, peripheral joining surface(s) 115 vacuum chamber 116.

In an embodiment of the invention, as can be seen in FIG. 3. showing a cross-sectional view 117 of the negative pressure therapy device, the device contains a cushion 100 in the form of an fluidly sealed chamber containing an inner urethane layer 114, an outer urethane layer 111, an adhesive layer 110 applied to the outer urethane layer 111. The cushion further consists of a foam layer 112 located inside the fluidly sealed chamber and a semi-rigid ribbon layer 113 as a backing to the foam layer 112. The adhesive layer 110 is preferably made of a biocompatible, non-toxic material to act as a mechanical anchor to inhibit motion of the device that could cause leakage of negative pressure and further, formation of skin damage for example blisters. The adhesive layer is of a thickness and tack selected so as to flow into surface anomalies to create and maintain an optimal seal and self-repair through multiple applications and removals.

The adhesive layer 110 is affixed to the cushion element 100 independently or in combination with one or more layers of material to for example a primer layer 125 and or an adhesion promoting layer 126 to achieve the desired preferential adhesion of the adhesive layer to the device while providing the desired releasable mechanical anchoring, sealing and cushioning properties of the adhesive layer to the user. Additionally, the releasable mechanical anchoring, sealing and cushioning properties of the adhesive layer 110 may be achieved by using a single adhesive material or a combination of materials.

Figure 7C:
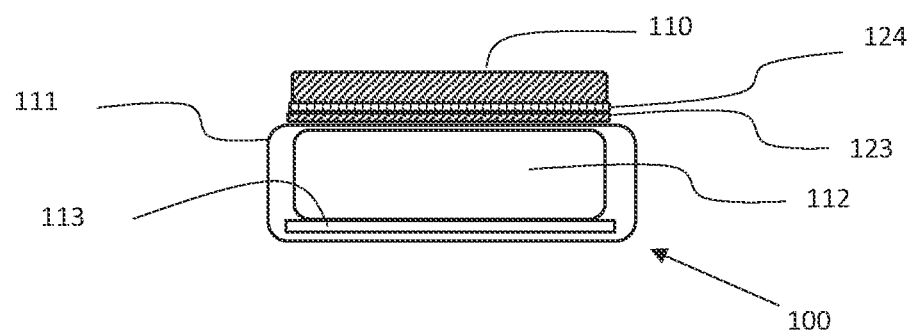
FIG. 7C is a cross-sectional view 117 of an illustrative embodiment of the cushion element 100 containing an adhesive layer 110, the outer layer of the fluidly sealed chamber 111, the foam layer element 112, the ribbon layer element 113, a primer layer 123 and an adhesive promoting layer 124.

FIG. 7a-7c show cross-sectional views (FIG. 3, 117) of the cushion element 100 with varied arrangements of materials making up the adhesive layer 110. For example, FIG. 7a shows a design wherein the cushion element 100 contains a single adhesive layer 110 located directly on the outer contact surface of the cushion element 100. In additional embodiments, FIG. 7b shows a design where the cushion element 100 contains a primer layer 123 located between the outer contact surface of the cushion element 100 and the single adhesive layer 110. And in yet a further embodiment, FIG. 7c shows a design where the cushion element 100 contains a primer layer 123 located on the outer surface of the cushion element 100 and an adhesive promoting layer 124 located between the primer layer 123 and the adhesive layer 110. The single adhesive layer element 110 being made of a silicone gel 125, a hydrogel 126 or any material of the like.

Figure 7D:
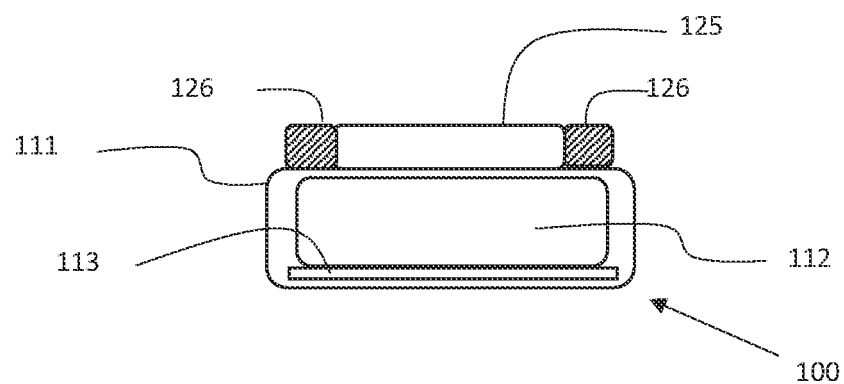
FIG. 7D is a cross-sectional view 117 of an illustrative embodiment of the cushion element 100 with an adhesive layer containing a hydrogel center layer 125 and silicone gel peripheral layer(s) 126, the outer layer of the fluidly sealed chamber 111, the foam layer element 112 and the ribbon layer element 113.
Figure 7E:
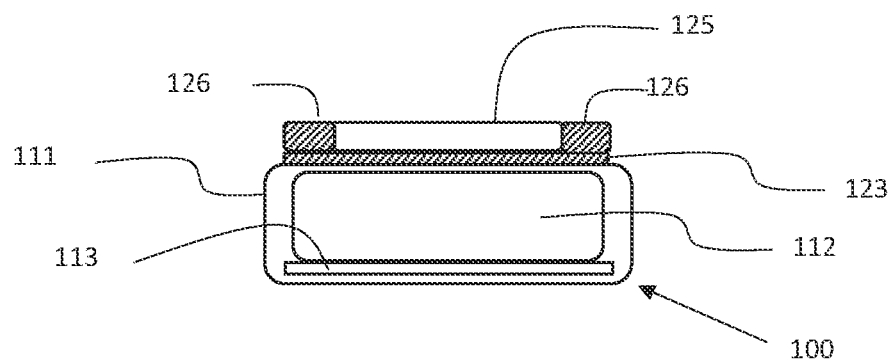
FIG. 7E is a cross-sectional view 117 of an illustrative embodiment of the cushion element 100 with an adhesive layer containing a hydrogel center layer 125 and silicone gel peripheral layer(s) 126, the outer layer of the fluidly sealed chamber 111, the foam layer element 112, the ribbon layer element 113 and a primer layer 123.
Figure 7F:
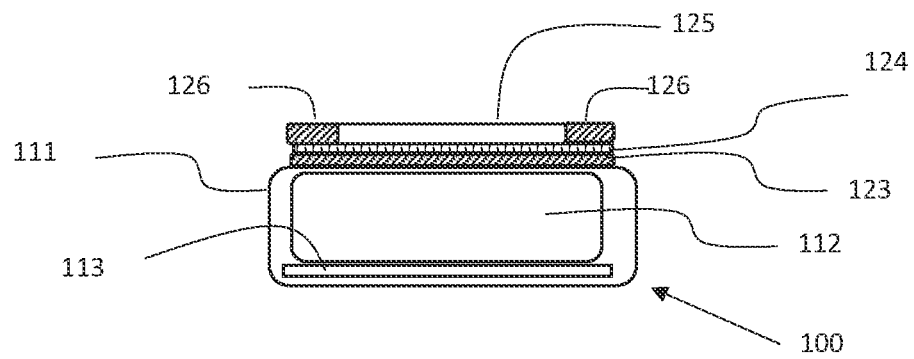
FIG. 7F is a cross-sectional view 117 of an illustrative embodiment of the cushion element 100 with an adhesive layer containing a hydrogel center layer 125 and silicone gel peripheral layer(s) 126, the outer layer of the fluidly sealed chamber 111, the foam layer element 112, the ribbon layer element 113, a primer layer 123 and an adhesive promoting layer 124.

In an embodiment where the adhesive layer contains varied layers of materials, the application of a primer layer, adhesive promoting layer or both may be confined to regions where the greatest stress from repeated application and removal of the negative pressure therapy device is observed. For example, FIG. 7j shows a cross sectional view of the cushion element (FIG. 3, 117) wherein the cushion element 100 contains a primer layer 123 located on the outer corners of the contact surface of the cushion element 100 and an adhesive layer 110 spanning the contact surface of the cushion element 100 over the corners of the cushion element 100 coated with the primer layer 123.

Figure 7G:
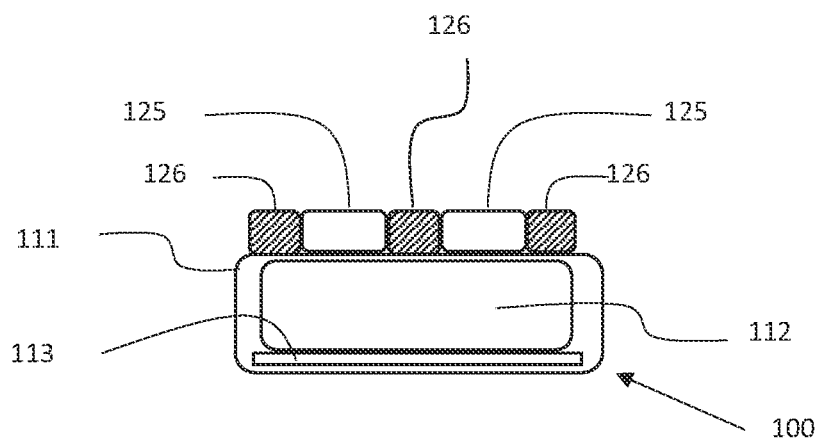
FIG. 7G is a cross-sectional view 117 of an illustrative embodiment of the cushion element 100 with an adhesive layer containing a silicone gel center 126 and silicone gel outer layers 126 and hydrogel layers 125 peripheral to the center silicone gel layer and bordered by the outer silicone gel layers, the outer layer of the fluidly sealed chamber 111, the foam layer element 112 and the ribbon layer element 113.
Figure 7H:
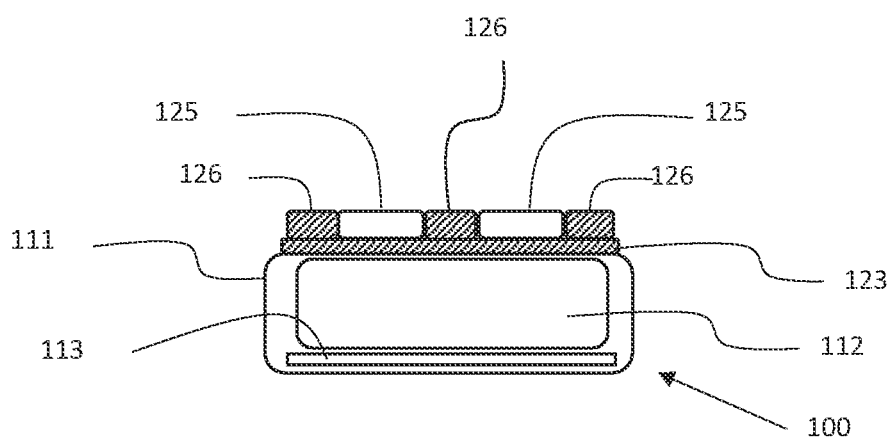
FIG. 7H is a cross-sectional view 117 of an illustrative embodiment of the cushion element 100 with an adhesive layer containing a silicone gel center 126 and silicone gel outer layers 126 and hydrogel layers 125 peripheral to the center silicone gel layer and bordered by the outer silicone gel layers, the outer layer of the fluidly sealed chamber 111, foam layer element 112, the ribbon layer element 113 and a primer layer 123.
Figure 7I:
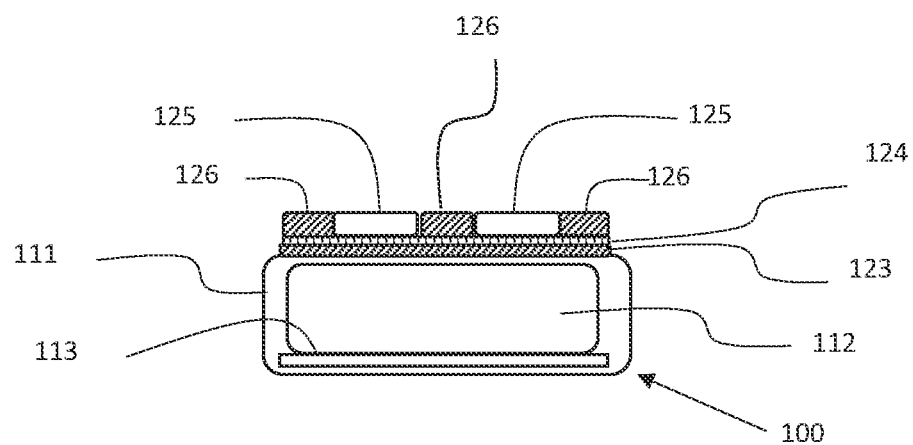
FIG. 7I is a cross-sectional view 117 of an illustrative embodiment of the cushion element 100 with an adhesive layer containing a silicone gel center 126 and silicone gel outer layers 126 and hydrogel layers 125 peripheral to the center silicone gel layer and bordered by the outer silicone gel layers, the outer layer of the fluidly sealed chamber 111, foam layer element 112, the ribbon layer element 113, a primer layer 123 and an adhesive promoting layer 124.
Figure 7J:
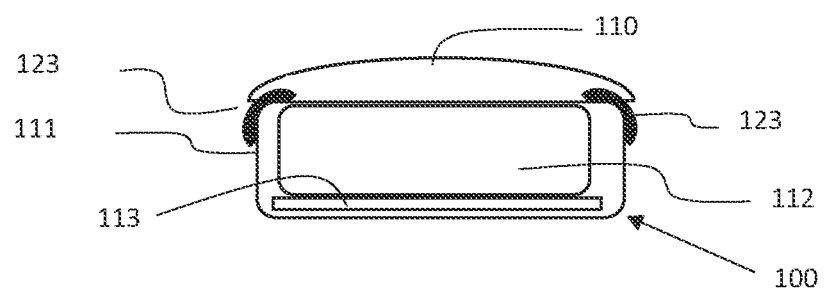
FIG. 7J is a cross-sectional view 117 of an illustrative embodiment of the cushion element 100 with an adhesive layer 110 with primer layers located at the corners of the outer layer of the fluidly sealed chamber 111, the foam layer element 112 and the ribbon layer element 113.

The invention the adhesive layer may contain configurations where varied adhesive materials are placed adjacent to one another on the outer contact surface of the cushion element 100. For example, in FIGS. 7d, 7e and 7f, showing a cross-sectional view 117 of the cushion element, a hydrogel layer 126 is applied to the center of the cushion element 100 and contains peripheral layers of a silicone gel 126. The aforementioned configuration can be applied directly to the outer surface of the cushion element 100 as seen in FIG. 7d, in a combination with a primer layer 123 as seen in FIG. 7e, or in combination with a primer layer 123 and an adhesion promoting layer 124 as seen in FIG. 7f.

Where the adhesive layer contains varied configurations of adhesive material, a silicone gel layer 125 may be place in the center of the outer contact surface of the cushion element 100 with peripheral layers of a hydrogel 126 with further peripheral layers of a silicone gel, as seen in FIG. 7g, FIG. 7h and FIG. 7i. The aforementioned configuration can be applied directly to the outer surface of the cushion element 100 as seen in FIG. 7g, in a combination with a primer layer 123 as seen in FIG. 7h, or in combination with a primer layer 123 and an adhesion promoting layer 124 as seen in FIG. 7i.

The cushion element 100 contains an outer urethane layer 111 to which an inner urethane layer 114 is adhered through creating a peripheral joining surface. The peripheral joining surface 115 creates fluidly sealed joints 115 and an air-tight seal to form the fluidly sealed chamber of the cushion element. The peripherally joining surface(s) 115 are created on surfaces of the cushion furthest away from the contact surface of the therapy area to minimize the possibility of edges of the contacting the surface of the skin and causing irritation. The space between the inner urethane layer 114 and outer urethane layer 111 form a fluidly sealed chamber that contains a fillable volume. The fillable volume may be span the entirety of the cushion or contain chambers. Further, the fillable volume may contain compressible elastic-type materials such as air, gel, beads, microspheres, foam, slurries or a combination in partial or in whole.

The fillable volume of the cushion 100 may further contain a foam layer element 112. The foam layer element may be selected from a range of densities for specific regional compliance providing higher or lower rebound rates further managing the force applied on the contact surface of the patient when the therapy device is applied. The foam layer 112 may further be backed by a semi-rigid ribbon layer 113. The ribbon layer 113 is located inside the cushion 100, toward the inner portion of the therapy device 116 furthest away from the contact surface of the therapy area. The ribbon layer displaces the load of the dome/chamber 116 evenly through the cushion element.

Figure 4:
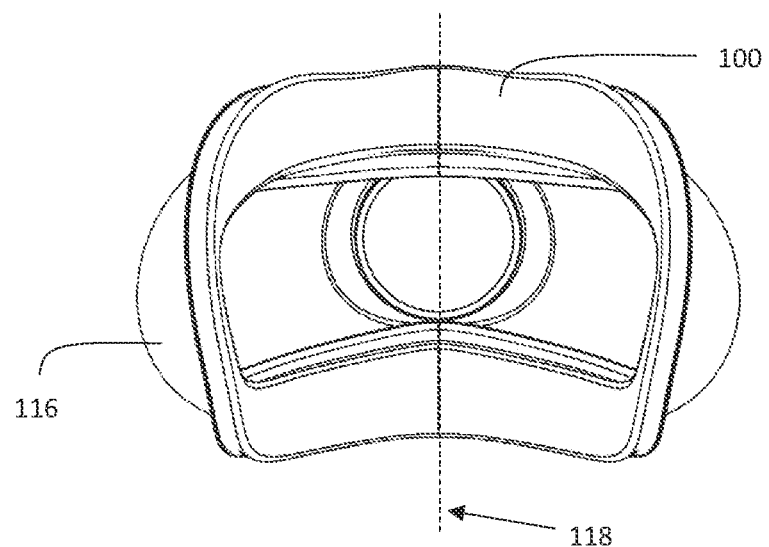
FIG. 4. is a three dimensional rear view of an illustrative embodiment of the vacuum chamber/dome 116 including the cushion element 100 with a vertical bisecting line 118 for illustration purposes in FIG. 5.
Figure 5:
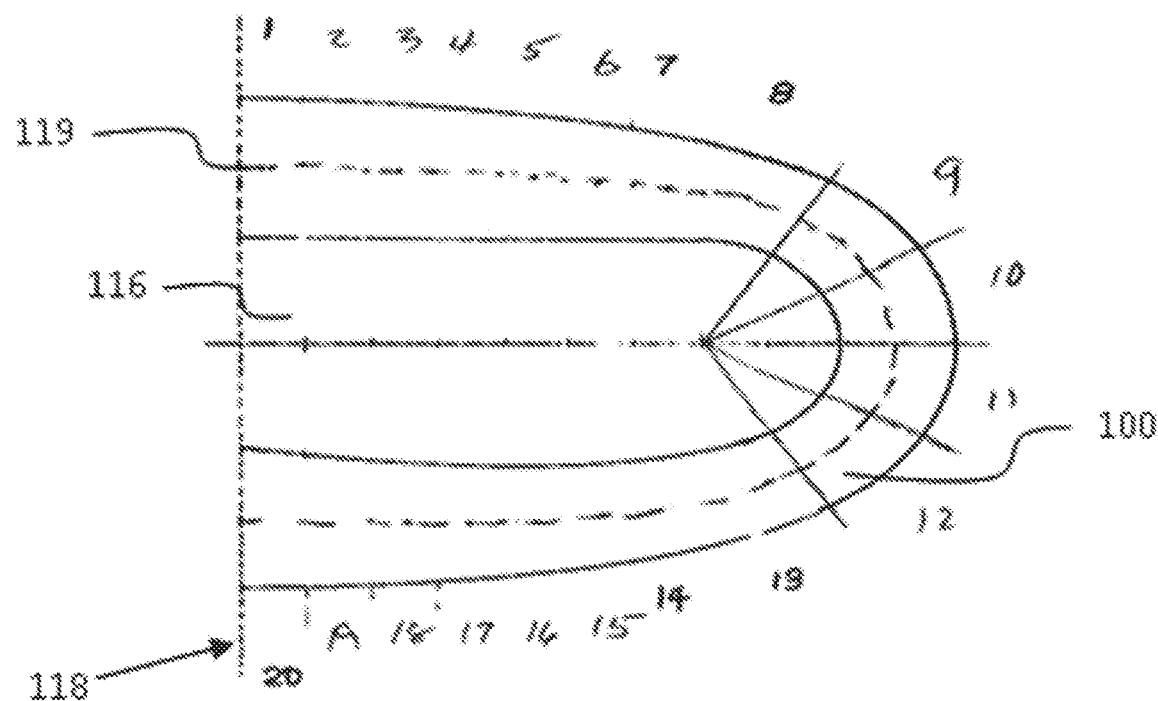
FIG. 5 is a two dimensional rear view of an illustrative embodiment of half the therapy device, bisected along the vertical axis 118 and FIG. 5, 118, showing the flattened half of the chamber/dome 116 including a flattened cushion 100, the cushion element further having a dashed line 119 approximately following the curvature of the cushion as an example of a contact location of the vacuum chamber dome on the opposite side of the cushion element and the contact surface of the cushion element divided into stations 1-20 for graphical representation in FIG. 6.

The cushion 100 is designed to accommodate variations in station load upon placement of the therapy device on a subject and application of a therapeutic level of negative pressure. This is accomplished by device design and structural elements that anticipate known anatomical features as well as structural elements that can accommodate surface variations that occur during use. FIG. 4, showing the rear of the therapy device with the chamber/dome feature 116 and cushion element 100 has line bisecting the device 118 for purposes of FIG. 5. In order to further graphically illustrate the cushioning feature(s) of the device, FIG. 5 shows a flattened/two dimensional representation of half of the therapy device with chamber/dome 116 and cushion element 100, with the bisecting line 118 as seen in FIG. 4 and a dashed line through the center of the cushion 119 showing the approximate location of the chamber/dome on the rear of the cushion element. The flattened half of the cushion 100 is approximately sectioned into 20 stations beginning at station 1, located closest to the upper middle section of the device that makes contact with the chin of the user, progressing through stations 8-13 traveling over approximately over the mandible and goinion approaching the ear and down to the neck toward station 20 located at the bottom portion of the half of cushion located approximately at the middle of the neck of the user.

Figure 6A:
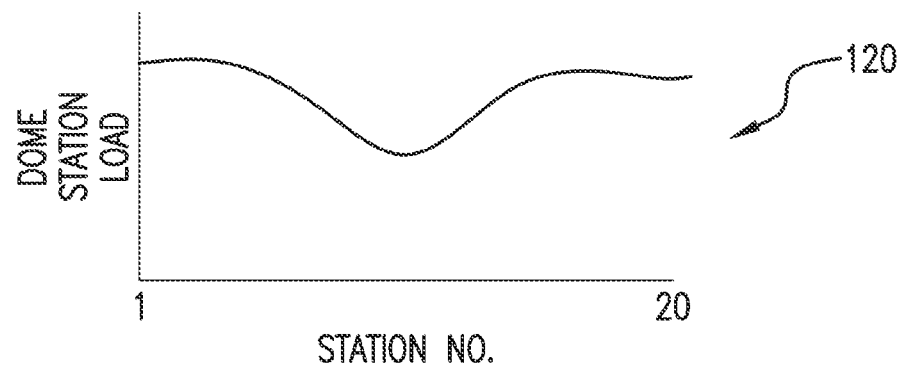
FIG. 6A is a graphical representation of the station load along stations 1-20 in FIG. 5 without a cushion element present 120.

Absent features, for example a cushion (and structural features therein) to balance the contact pressure of the device when a therapeutic level of negative pressure is applied, a user would experience varied contact pressures, for example, lower contact pressure in regions where the cross section of the dome decreases due to the non-symmetric shape of the dome for example at the tips of the oval shaped dome/at the ends of the device, specifically through stations 8-13, FIG. 5. Further as can be seen in FIG. 6A, 120, which is a graphical representation of an un-cushioned therapy device with the dome station load in the Y axis and the station number on the X axis, as one approaches the tip of the oval as in FIG. 5 stations 8-13 the dome station load decreases.

Figure 6B:
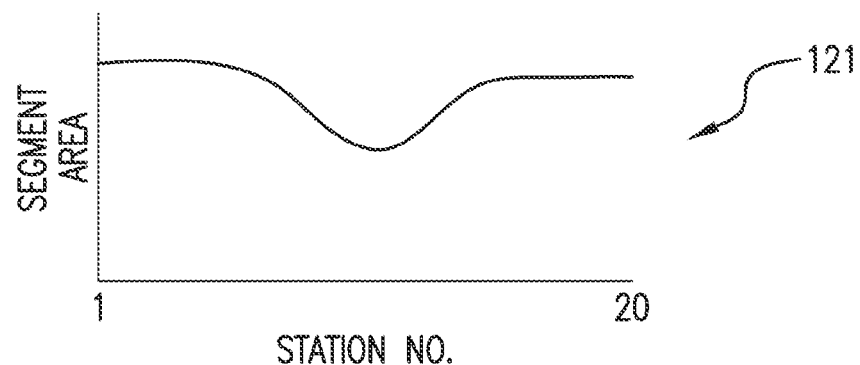
FIG. 6B is a graphical representation of a cushion configured to accommodate station loads along contact stations 1-20 where design elements of the cushion (for example, decreasing perpendicular width and subsequent section area, approaching and through stations 8-13) increases pressure at stations 8-13 toward the end of the oval 121.
Figure 6C:
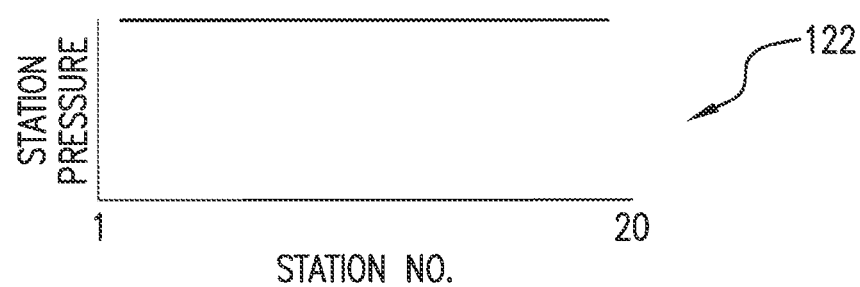
FIG. 6C is a graphical representation the equalized station load upon application of the cushion element 100 to the chamber 116 showing alleviation of station pressure variation due to design attributes of cushion element 122.

In certain embodiments the perpendicular width of the cushion element is therefore varied to increase or decrease the contact pressure at certain stations. A decrease in the perpendicular width reduces the segment area ultimately increasing the contact pressure for that section when a therapeutic level of negative pressure is applied. For example in FIG. 5 as one approaches stations 8-13 one can see the perpendicular width decreases. FIG. 6B, 121 further shows a graphical representation of the cushion segment area on the Y axis and the station number on the X axis, as one approaches stations 8-13 the segment area decreases. Therefore, when one combines a known variation in dome station load with a design feature configured to accommodate the variation a lowest possible station pressure variation is achieved.

Cushion balancing may also be accomplished through variation in other structural elements of the cushion both locally and throughout the contact surface, for example foam thickness, foam density, ribbon stiffness, and fluidly sealed chamber pressure alone, whole or in part. In a preferred embodiment the structural elements including the aspect ratio of the cushion may change to provide minimal variation in contact pressure wherein the contact pressure is approximately 1.2 times that of the applied vacuum at all contact points of the cushion element.

Structural embodiments of the apparatus may vary based on the size of the device and the description provided herein is a guide to the functional aspects and means.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims:

What is claimed is:

1. A method of forming a therapy device configured for the administration of negative pressure upon an external location of a human overlying the anterior triangle of the neck, the method comprising:
    providing a vessel configured to define a chamber at the external location of the human;
    providing a cushion element comprising a fluidly sealed chamber, a non-flowing material positioned within the fluidly sealed chamber, the non-flowing material configured to provide mechanical support to the fluidly sealed chamber to prevent regional collapse of the fluidly sealed chamber when the therapy device is mated to the human and a therapeutic level of negative pressure is applied within the vessel, and
    providing a semi-rigid ribbon layer positioned within the fluidly sealed chamber and on a surface of the non-flowing material; the semi-rigid-ribbon layer providing rigidity which is configured to displace a load of the fluidly sealed chamber when the therapeutic level of negative pressure is applied,
    affixing the cushion element on a peripheral edge of the vessel to define a skin contact surface at the external location such that the cushion element lies between the peripheral edge of the vessel and the skin contact surface.

2. A method according to claim 1, wherein the cushion element is formed by affixing the ribbon layer on the non-flowing material, followed by sealing the non-flowing material and the ribbon layer within the cushion element to form the fluidly sealed chamber.

3. A method according to claim 2, wherein the cushion element is formed prior to affixing the cushion element on the peripheral edge of the vessel.

4. A method according to claim 2, wherein the cushion element is formed in situ on the peripheral edge of the vessel.

5. A method according to claim 2, wherein a first surface of the cushion element and a second surface of the cushion element are formed as separate surfaces that are affixed to one another at a joining surface to form the fluidly sealed chamber, wherein the joining surface is configured to not contact the skin contact surface at the external location when the therapy device is mated to the human and a therapeutic level of negative pressure is applied within the vessel.

* * * * *